United States Patent
Chitiboi et al.

(10) Patent No.: US 12,393,827 B2
(45) Date of Patent: Aug. 19, 2025

(54) LATE GADOLINIUM ENHANCEMENT ANALYSIS FOR MAGNETIC RESONANCE IMAGING

(71) Applicant: SIEMENS HEALTHINEERS AG, Forchheim (DE)

(72) Inventors: Teodora Marina Chitiboi, Hamburg (DE); Puneet Sharma, Princeton Junction, NJ (US); Athira Jane Jacob, Plainsboro, NJ (US); Ingmar Voigt, Erlangen (DE); Mehmet Akif Gulsun, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 766 days.

(21) Appl. No.: 17/645,463

(22) Filed: Dec. 22, 2021

(65) Prior Publication Data

US 2023/0196557 A1  Jun. 22, 2023

(51) Int. Cl.
*G06N 3/045* (2023.01)
*G06N 3/08* (2023.01)
(Continued)

(52) U.S. Cl.
CPC .............. *G06N 3/045* (2023.01); *G06N 3/08* (2013.01); *G06T 5/60* (2024.01); *G06T 7/0012* (2013.01);
(Continued)

(58) Field of Classification Search
CPC ......... G06T 7/0012; G06T 2207/10088; G06T 2207/20081; G06T 2207/20084;
(Continued)

(56) References Cited

U.S. PATENT DOCUMENTS 10,649,053 B2 * 5/2020 Hu .................. A61B 5/339
11,308,613 B2 * 4/2022 Chitiboi ................ G06T 7/11
(Continued)

FOREIGN PATENT DOCUMENTS

EP         3576100 A1      12/2019

OTHER PUBLICATIONS

Cho, Jung Sun, et al. "A network-based "phenomics" approach for discovering patient subtypes from high-throughput cardiac imaging data." JACC: Cardiovascular Imaging 13.8 (Aug. 2020): 1655-1670.
(Continued)

*Primary Examiner* — Tom Y Lu

(57) ABSTRACT

For training for and performance of LGE analysis, multi-task machine-learning model is trained to output various cardiac tissue characteristics based on input of LGE MR data. The use of segmentation may be avoided or limited, resulting in a greater number of available training data samples, by using radiology clinical reports with LGE information as a source for samples. The multi-task model may be trained to output cardiac tissue characteristics using radiology clinical reports with LGE information with no segmentation or with segmentation for only a subset of the training samples. By training for multiple tasks, the accuracy of prediction for each task benefits from the information for other tasks. The trained model outputs values of characteristics for multiple tasks, such as extent of enhancement, type of enhancement, and localization of enhancement. Other tasks may be included, such as disease classification. Other inputs may be used, such as also including sensor data and/or cardiac motion.

22 Claims, 3 Drawing Sheets

(51) Int. Cl.
      *G06T 5/60*       (2024.01)
      *G06T 7/00*       (2017.01)
      *G16H 30/20*     (2018.01)

(52) U.S. Cl.
      CPC ... *G16H 30/20* (2018.01); *G06T 2207/10088* (2013.01); *G06T 2207/20081* (2013.01); *G06T 2207/20084* (2013.01); *G06T 2207/30048* (2013.01)

(58) Field of Classification Search
      CPC ... G06T 2207/30048; G06T 5/60; G06N 3/08; G06N 3/084; G06N 3/045; G16H 30/20; G16H 50/70; G16H 30/40; G16H 50/20
      See application file for complete search history.

(56) References Cited

U.S. PATENT DOCUMENTS

| | | | |
|---|---|---|---|
| 2019/0290232 A1* | 9/2019 | Garg | A61B 6/037 |
| 2022/0101530 A1* | 3/2022 | Trayanova | G16H 50/20 |
| 2022/0309342 A1* | 9/2022 | Borgohain | G06N 3/047 |
| 2022/0343475 A1* | 10/2022 | Zhang | A61B 5/055 |
| 2023/0394670 A1* | 12/2023 | Trayanova | G06T 7/12 |

OTHER PUBLICATIONS

Sailesh Conjeti, et al. "Medical Image Analysis" Science Direct. vol. 34, 2016, Abstract, ISSN 1361-8415,https://doi.org/10.1016/j.media.2016.05.010.

\* cited by examiner

LATE GADOLINIUM ENHANCEMENT ANALYSIS FOR MAGNETIC RESONANCE IMAGING

BACKGROUND

The present embodiments relate to delayed gadolinium enhancement (LGE) analysis for magnetic resonance imaging (MRI). The quantitative and qualitative analysis of LGE MRI for the presence of nonviable scar tissue has an essential role in the diagnosis and management of ischemic and non-ischemic cardiovascular diseases. In clinical practice, LGE analysis is typically a manual or semi-automatic process. Automated or manual segmentation of the myocardium and of the scar tissue is performed. The user may be involved in contour correction and/or the selection of healthy or fibrotic reference regions.

Recent machine learning and deep learning approaches focus on the automatic quantification of the myocardium and scar from LGE MRI. The main challenge for these approaches is collecting sufficient annotated data that is representative across different pathologies and anatomical diversity, as well as across various LGE sequences, specific scan parameters, and image qualities that occur in clinical practice. Acquiring ground truth segmentation labels for LGE data is an additional challenge because the annotation process is a complex task relying on specific clinical expertise and can typically only be carried out by specialists with extensive clinical training. Another challenge is the large inter-user variability in the manual segmentation. Users tend to disagree on the exact delineation of scar regions, resulting in less definitive training data.

SUMMARY

Systems, methods, and instructions on computer readable media are provided for training for and performance of LGE analysis. A multi-task machine-learning model is trained to output various cardiac tissue characteristics based on input of LGE MR data. The use of segmentation may be avoided or limited, resulting in a greater number of available training data samples, by using radiology clinical reports with LGE information as a source for samples. The multi-task model may be trained to output cardiac tissue characteristics using radiology clinical reports with LGE information with no segmentation or with segmentation for only a subset of the training samples. By training for multiple tasks, the accuracy of prediction for each task benefits from the information for other tasks. The trained model outputs values of characteristics for multiple tasks, such as extent of enhancement, type of enhancement, and localization of enhancement. Other tasks may be included, such as disease classification. Other inputs may be used, such as also including sensor data and/or cardiac motion.

In a first aspect, a method is provided for LGE analysis for an MR imager. LGE MR data representing a patient is acquired. (1) An extent of enhancement, (2) a type of enhancement, and (3) a localization of enhancement of cardiac tissue are determined. A machine-learned model with separate output branches for the extent, the type, and the localization performs the determination. The output branches are responsive to a latent representation from input of the LGE MR data to the machine-learned model. The extent, type, and localization are displayed.

In one embodiment, the extent is a presence or absence of the enhancement, the type is focal or diffuse, and the localization is localized within a part of the myocardial wall region or not. The extent, type, and localization may be determined for each of multiple regions of a heart model.

In another embodiment, the machine-learned model is a deep learnt neural network. For example, the deep learnt neural network is an encoder receiving the input of the LGE MR data and outputting the latent representation and three decoders forming the separate output branches.

In other embodiments, a disease classification for the cardiac tissue is determined based on another output branch and the latent representation.

In some embodiments, the machine-learned model was trained using radiology clinical reports with LGE information. For example, the machine-learned model was trained using the radiology clinical reports with LGE information without segmentation of a boarder of a scar in the cardiac tissue. In other examples, the machine-learned model was jointly trained with losses for the extent, type, and localization. The machine-learned model may have been jointly trained with the losses for the extent, type, and localization and another loss for a subset of the samples based on segmentation of a scar in the cardiac tissue.

In one embodiment, a saliency map is generated using at least one of the separate branches of the machine-learned model.

According to another embodiment, the determination is with input of (a) the LGE MR data and (b) images showing cardiac motion or deformation and/or sensor data to the machine-learned model. The latent representation is based on (a) the LGE MR data and (b) the images showing cardiac motion or deformation and/or sensor data.

In a second aspect, a medical system is provided for LGE analysis. A memory is configured to store LGE data from an MR imager and instructions. An image processor is configured, by execution of the instructions, to apply a machine-learned multi-task network to the LGE data. The machine-learned multi-task network is configured to output values for first and second cardiac tissue characteristics in response to the application. A display is configured to display the values for the first and second cardiac tissue characteristics.

In one embodiment, the machine-learned multi-task network is an encoder configured to generate a latent representation of the LGE data and first and second decoders configured to output the values for the first and second cardiac tissue characteristics, respectively, based on the latent representation.

According to an embodiment, the first and second cardiac tissue characteristics are different ones of extent of enhancement, type of enhancement, and localization of enhancement.

In yet another embodiment, the machine-learned multi-task network further includes a classifier configured to output a classification of disease in response to the application.

In another embodiment, the machine-learned multi-task network is configured to receive the LGE data and cardiac motion imaging data. The output of the values is in response to application to the LGE data and the cardiac motion imaging data.

In one embodiment, the machine-learned multi-task network was trained using radiology clinical reports with LGE information without segmentation of scars for most of the samples of the training data.

In various embodiments, the image processor is configured to determine the output values for each of a plurality of standardized heart regions.

In a third aspect, a method is provided for machine training a model. Multiple LGE characteristics of hearts are extracted from radiology clinical reports with LGE information for a plurality of patients. A multi-task model is machine trained to receive LGE image data and output values for the multiple LGE characteristics. Training data for the machine training includes the extracted LGE characteristics as ground truth. The machine trained multi-task model is stored.

In one embodiment, automated extraction from the radiology clinical reports with LGE information is performed with natural language processing or textual pattern matching.

According to another embodiment, an image processor segments scar tissue represented in the LGE data for a subset of the training data. The machine training includes machine training with first and second tasks of the multi-task model being cardiac tissue characterization and a third task of the multi-task model being segmentation. A loss for the machine training is based on the first and second tasks for the training data without the segmented scar tissue and based on the first, second, and third tasks for the training data with the segmented scar tissue.

Any one or more of the aspects described above may be used alone or in combination. Any aspects of one of method, system, or computer readable media may be used in the others of method, system, or computer readable media. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS

A weakly supervised approach is used for LGE detection, quantification, and/or classification. A multi-task model solves for multiple patient modeling problems as the multiple tasks. The weakly supervised approach to training for LGE quantification does not require fully segmented ground truth images but relies on segment-level findings typically noted in the radiology clinical report. This approach can benefit from clinical image data accompanied by clinical reports, which typically does not have a segmentation ground truth. As a result, the amount of data available for training is increased. This approach circumvents some of the challenges related to ground truth segmentation masks by relying entirely or mostly on the clinical reports for ground truth.

The multi-task machine-learned model may have access to more context information to automatically solve the problem as compared to training separate networks for each task. Since all tasks share some information (e.g., a significant amount of computation in the form of the same features), the inference may be faster than having separate solutions for each task and running them in sequence and/or in parallel. Since the consequent task-specific parts of the network are supported by common features, the model complexity may be reduced as compared to providing separate models for the separate tasks. The multi-task machine-learned model may have better accuracy as compared to training separate networks for each task. Each task benefits from training for the other tasks. As a result of efficiency, performance, and/or flexibility, more accurate results are provided using less computational power and less memory resources.

Figure 1:
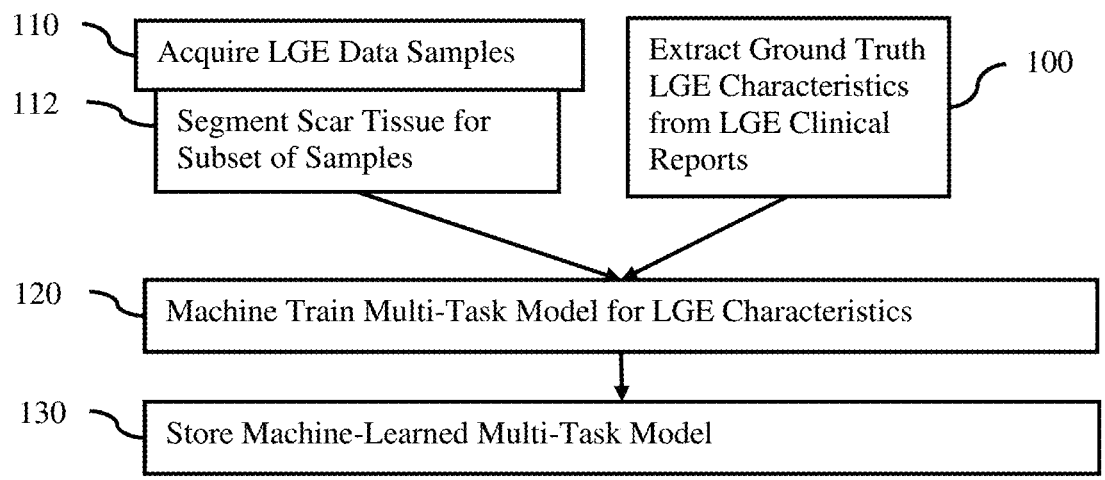
FIG. 1 is a flow chart diagram of one embodiment of a method for machine training a multi-task model for LGE analysis.

FIG. 1 is a flow chart diagram of one embodiment of a method for machine training a multi-task model for LGE analysis. The model is trained to estimate values for different tissue characteristics, allowing training data based on radiology clinical reports where LGE scanning was used or which include information from LGE images radiology clinical reports with LGE information with limited or no segmentation. A much larger number of training samples may be gathered where accurate segmentation is not needed.

The training is performed by an image processor using training data (e.g., LGE data samples and corresponding ground truth values for characteristics) stored in a database. Other devices may be used.

The acts are performed in the order shown (numerical or top-to-bottom) or other orders. For example, act 110 is performed prior to or simultaneously with act 100. Additional, different, or fewer acts may be provided. For example, act 112 for segmenting is not performed.

In act 100, a processor or user extracts multiple LGE characteristics of hearts from radiology clinical reports with LGE information for a plurality of patients. For each patient and corresponding training data sample, values for two or more characteristics are extracted. For example, values for the extent (e.g., presence or absence of LGE enhancement or % of scar to non-scar tissue), type (e.g., focal or diffuse), and/or localization (e.g., localized within the heart wall or not or sub-endocardial, epicardial, mid-wall, or transmural) are extracted. Values for other characteristics available from radiology clinical reports with LGE information and/or other sources may be extracted.

Figure 3:
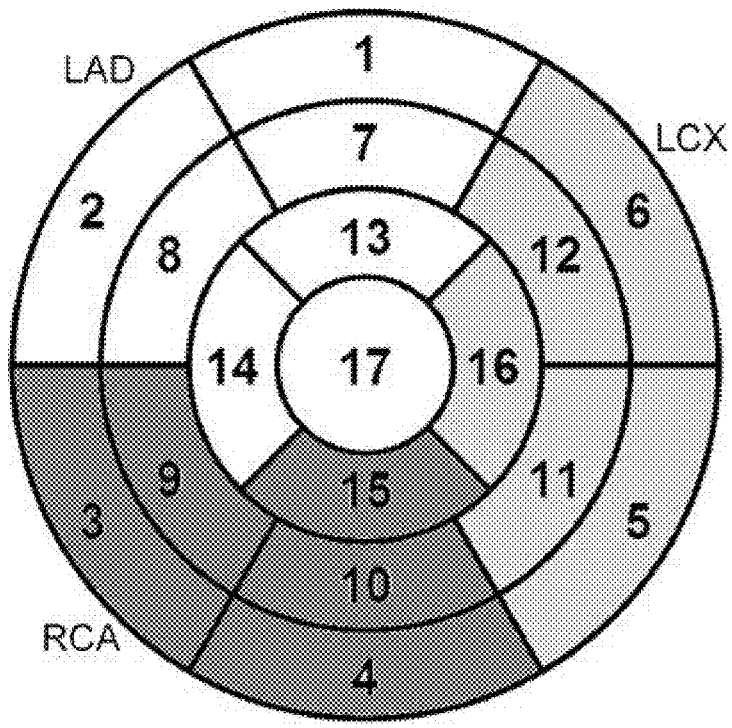
FIG. 3 is an example heart model with displayed LGE extent information.

Each characteristic represents the entire heart or patient. Alternatively, some or all the characteristics are extracted for each of different regions of the heart. For example, a standard heart model (e.g., American Heart Association (AHA) 16-segment heart model) defines multiple different heart regions. FIG. 3 shows an example AHA 16-segment heart model. Values may be extracted for each of the heart regions. In one embodiment, the radiology clinical reports with LGE information are used to extract: presence or absence of LGE enhancement for each individual segment in the standard AHA 16-segment (or similar) model, extent of the scar region per given territory as a percentage (x %), focal vs. diffuse, and localization within the wall (e.g., sub-endocardial, epicardial, mid-wall, or transmural). Any number of characteristics may be used. Additional, different, or fewer characteristics may be used.

The values are extracted from radiology clinical reports with LGE information. The radiology clinical reports with LGE information may include textual or image-based indications (e.g., annotations) of values of the characteristics. Segmentation of borders may not be in the radiology clinical reports with LGE information. For example, the LGE clinical report may include free text indicating which, if any, AHA segments have scar tissue present, the %, the type (e.g., focal vs. diffuse), and the localization. Segments not mentioned in the LGE clinical report may be assumed to not have scar tissue. Other sources of information to derive values of the characteristics may be used, such as using algorithms or machine-learned models to extract from images and/or information from electronic medical records.

In one embodiment, the extraction from the radiology clinical reports with LGE information for multiple patients is automated. A processor uses natural language processing or textual pattern matching to extract. The values for the characteristics may be extracted using natural language processing (NLP) algorithms or simple pattern matching (e.g., word or text patterns).

The extracted values for the cardiac tissue characteristics (e.g., for scar tissue characteristics) are used as ground truth data. For each sample (e.g., each past patient), the values are extracted and used as ground truth for the corresponding tasks in training the multi-task model. The ground truth data may be organized in several detection and classification tasks. A deep learning network may be trained to solve for all these tasks simultaneously or sequentially.

In act 110, LGE data is acquired. The training data includes the ground truth as well as the LGE data as samples. For each patient, the input and output (ground truth) are gathered. Each sample includes paired input and output. The LGE data is obtained as the input to use for the model.

The LGE data is image data representing the heart of the patient. An LGE MR protocol is followed to scan the patient. The resulting LGE data is obtained. The LGE data may be a reconstruction of the scanned region (e.g., voxels or multiple slices) or images rendered to a display (e.g., pixels).

The LGE data is acquired from the electronic medical records of the patients, such as in an image archival system or electronic patient medical record. The LGE data may be from a picture archiving and communications system (PACS). In other embodiments, the LGE data is acquired from an MR imager and/or database.

The LGE data may be pre-processed. The LGE stack of slices are transformed and/or projected into a known frame of reference. For example, several landmarks are identified in the images, such as identifying or locating the left ventricle (LV) and right ventricle (RV) base and apex, the RV insertion points, and valve positions. These landmarks are used to identify an image orientation. The LGE image data for each patient is, based on the orientation, rotated and cropped to fit a standard orientation and field of view. Scaling may be performed.

In one embodiment, none of the training data includes segmented tissue. A border, pixel locations, or voxel locations for specific tissue (e.g., scar or lesion) is not delineated, so not used to train the multi-task model. While heart regions or segments of a model may be used, these regions or segments are for parts of the heart without reference to any delineation of abnormality, not a segmentation of a specific structure, such as not a segmentation of scar tissue.

In other embodiments, scar tissue or other cardiac tissue is segmented in act 112. The acquired LGE data samples may include segmentations or cardiac tissue delineations. Alternatively, a user (e.g., radiologist) or image processor segments. For example, an image processor segments scar tissue represented in the LGE data for some of the training data. In one embodiment, any approach, such as full width, half maximum (FWHM) or intensity thresholding with various standard deviations, are used to segment the LGE data. Samples with segmentation are provided in the training database. The results of segmentation are reviewed by a specialist, who choses only the most precise of the results. These are then included in the training set. The segmentation masks are paired with the clinical reports or ground truth extracted from the clinical reports and the input LGE image data.

The segmentation is provided or created for a subset of the training data. Rather than segmenting for all samples, most of the samples are without segmentation. Some, such as fewer than 50%, 25%, 10% or 5%, have segmentation of one or more locations of scar tissue or other lesions. Alternatively, no segmentation is provided for any of the samples of the training data.

In act 120, an image processor machine trains a multi-task model. The model is trained to receive LGE image data, with or without other data, and to output values for multiple LGE characteristics. The training data obtained in act 100 provides values for the extracted LGE characteristics, which values or characteristics are used as the ground truth in machine training given the input.

For training the machine-learned model, the machine learning model arrangement is defined. The definition is by configuration or programming of the learning. The number of layers or units, type of learning, and other characteristics of the model are controlled by the programmer or user. In other embodiments, one or more aspects (e.g., number of nodes, number of layers or units, or type of learning) are defined and selected by the machine during the learning. Training data, including many samples of the input LGE data and the corresponding ground truths (i.e., values of the characteristics), is used to train. The relationship of the input to the output is machine learned. Once trained, the machine-learned model (machine-learned network) may be applied to estimate the characteristics from input LGE data for a patient.

Figure 2:
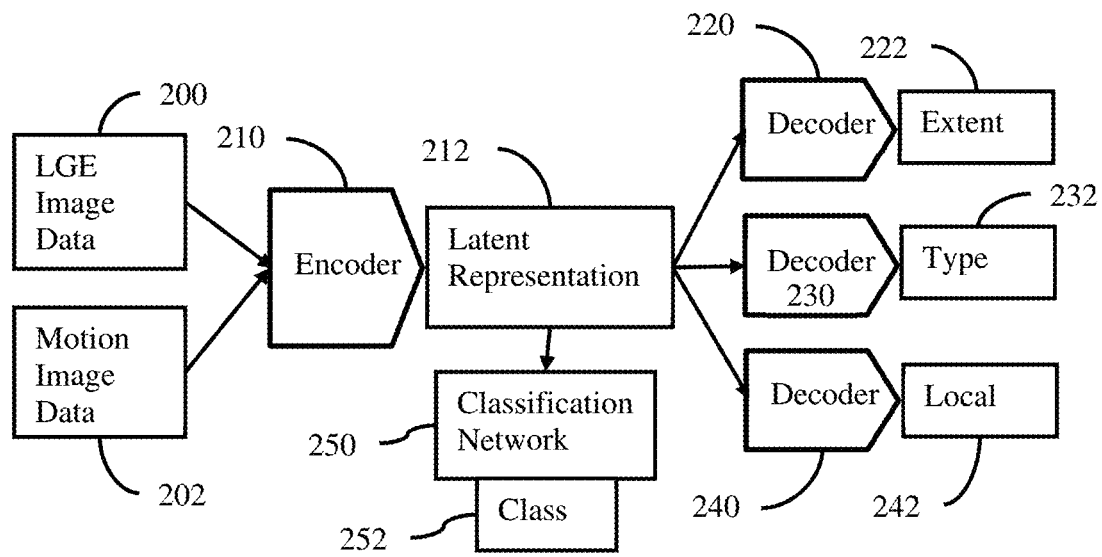
FIG. 2 is a block diagram of one embodiment of a machine-learned or machine learning model for LGE analysis.

FIG. 2 shows an example model for machine training. The model is a neural network formed from an encoder 210 and multiple decoders 220, 230 240. A classification network 250 is also included. Additional, different, or fewer components of the model may be provided. For example, the classification network 250 is not included. As another example, the motion image data 202 and corresponding input to the encoder 210 is not provided. In other examples, additional, different, or fewer decoders 220, 230, 240 and corresponding tasks are provided.

The encoder 210 has one or more layers, such as ten or more layers, with any number of nodes in each layer. Each node may use any activation function. Any types of layers may be used. In one embodiment, a series of down sampling and convolutional layers are used, such as an encoder from a U-Net or image-to-image network. Max or other pooling layer layers may be included. Dropout layers may be used. The encoder 210 increases abstraction and decreases resolution. The final layer outputs a latent representation 212. Values for one or more features are output by the encoder 210 in response to input data, such as the LGE image data 200. The latent representation 212 are values for features at an abstracted level relative to the input LGE image data 200. This latent representation 212 is a fingerprint for the patient.

Each of the decoders 220, 230, 240 has a same structure or architecture. In alternative embodiments, one or all the decoders 220, 230, 240 have different structures than the others. The decoders 220, 230, 240 have inputs to receive the latent representation 212. The values of the features output by the encoder 210 are input to the decoders 220, 230, 240. The decoders 220, 230, 240 output the characteristics 222, 232, 242 in response to input of the latent representation 212.

The decoders 220, 230, 240 are neural networks but other models may be used. The neural networks are fully connected or convolutional networks. Any number of layers and nodes in layers may be used. Various layer arrangements may be used, such as sequential layers or densely connected layers. In one embodiment, some of the layers are convolutional layers. Pooling, up-sampling, down-sampling, dropout, or other layers may be used. One layer, such as an output layer, is a Softmax layer or other layer for outputting a classification. Other architectures may be used. Different numbers of stages, layers, parameters, and/or convolutions in a layer may be used. Various kernel sizes, combinations of layers, and/or types of layers may be used.

The classification network 250 is a neural network or other architecture. The classification network 250 has any number, type, and/or arrangement of layers. The classification network 250 may be a same or different architecture as the decoders 220, 230, 240. In one embodiment, the classification network is a convolutional neural network (CNN) with pooling layers. The classification network 250 includes an output layer (e.g., SoftMax) for outputting a class membership 252 based on input of the latent representation 212.

The model has an architecture defined to output the characteristics 222, 232, 242 and/or class 252 for an entire heart and/or for a given region. For example, different models are trained to output for different segments of the heart model. In other embodiments, one model is trained to output values for each or all the segments of the heart model, such as outputting the extent 222, type 232, and localization 242 characteristics for each segment of the 16-segments of the AHA heart model in response to input of the LGE image data 200. The classification network 250 is defined to output the class 252 for the entire heart without reference to the heart regions or segments. Heart model region-based class may be output.

All the tasks (e.g., different output branches formed by the decoders 220, 230, 240, and classification network 250) share the computation by the encoder 210. In alternative embodiments, one or more skip connections provide information from the input and/or intermediate layers of the encoder 210 to one or more of the decoders 220, 230, 240 and/or classification network 250. By sharing the encoder 210 and using the same latent representation 212, the model may operate more efficiently, and any given characteristic estimation may benefit from the training based on all the tasks of the model.

In FIG. 2, the example neural network is for multi-tasking analysis of the LGE images. Each task corresponds to a type of clinical question where the answer is potentially in available radiology clinical reports with LGE information. The image encoder 210 brings the LGE images into a low-dimensional latent representation 212 (i.e., a unique task-specific patient fingerprint). The multiple decoders 220, 230, 240 are specifically designed for each of the tasks of detecting extent 222 (e.g., the presence and/or extent of the enhancement on a per-segment basis), classifying the type 232 of lesion (e.g., focal or diffuse), and assessing the region's localization 242 within the wall. The tasks are solved simultaneously using the multi-task model.

The classification network 250 may not be used or provided in some embodiments. In other embodiments, the model is extended to include disease classification. The classification network 250 outputs a disease class 252 based on the latent space representation 212 of the LGE image data 200.

The image processor machine trains the model. The training learns weights, connections, filter kernels, and/or other learnable parameters of the defined architecture. Deep or another machine learning may be used. The weights, connections, filter kernels, and/or other parameters are the features being learned. For example, convolution kernels are features being trained. Using the training data, the values of the learnable parameters of the model are adjusted and tested to determine the values leading to an optimum estimation of the output given an input. Adam or another optimization is used to train.

FIG. 2 shows four patient modeling tasks (e.g., extent 222, type 232, localization 242, and class 252), but additional, fewer, and/or different tasks may be incorporated into this framework. The incorporation uses assigned features from the encoder 210 by branching out at appropriate locations in the architecture.

In multi-task learning, a single model is defined that includes multiple outputs. An aggregated objective is used for the multiple outputs in the training, so that the error in each task influences all the tasks. The training tries to perform each task at the same time, optimizing for the joint objective. The difference between the output and ground truth for a given input is determined for each of the outputs or tasks. The average or weighted average of the losses across the tasks are used to jointly train the model. The aggregated loss is used to optimize the values of the learnable parameters of the model. In alternative embodiments, progressive training of the tasks is used.

In one embodiment, available segmentations are used in the machine training. Where some of the samples in the training data include segmentation, the model may be defined to output segmentation in one branch. For example, a decoder is added with the task of output of the segmentation. The decoder includes upsampling, pooling, convolution, and/or other layers to convert the latent representation 212 into a spatial representation of the segmentation of the cardiac tissue at the same or different resolution as the LGE image data 200.

The machine training is for the multiple tasks (e.g., two or more characteristics) with the segmentation being another task. Full and weak supervised training is used. For one subset of training samples, the loss for the machine training is based on some of the tasks (e.g., all tasks but the segmentation) for the training data without the segmented scar tissue. For other training samples, the loss is based on all the tasks for the training data with the segmented scar tissue.

The model is trained by jointly learning from full and weak supervision. The segmentation may be included for some of the samples in training. The training may account for variance from the ground truth, such as where the ground truth segmentation is from automated algorithms. For example, the segmentation predictions from the model are compared with results from an existing traditional approach (i.e., ground truth). Those cases that show the maximum discrepancies are automatically added to the training set so that the model may be trained to better estimate the segmentation. The model can then be refined using some dedicated expert-annotated segmentation.

The training may be iterative. For example, a trained model processes unannotated data, providing outputs. A larger subset of training data may then be accepted as sufficiently accurate to be used for training. Similarly, the model is fine-tuned on the dedicated expert-annotated data, and the process is repeated until most of the original unannotated data is processed correctly. For the iterative addition of training data, subsets of the data with maximum discrepancy between the model prediction and traditional, heuristic based methods are chosen to add to the training data for refining the model. This narrows down the data requiring expert annotation or refinement.

In act 130, the machine-trained multi-task model is stored. The learned weights, connections, kernels, and/or other values of the learnable parameters of the model learned are stored with the architecture or as part of the model.

The stored model may be used or applied. Copies of the stored model may be used or applied by different servers, image processors, computers, MR scanners, or workstations. In application, the latent representation 212 is determined based on input LGE image data 200 for a patient. The output branches (e.g., decoders 220, 230, 240 and/or classification network 250) output the extent 222, type 232, localization 242, and/or class 252 for that patient based on the latent representation 212 for that patient. The values of the learned parameters of the model, as fixed after training, are used for application to a patient or different patients (i.e., unseen data).

Figure 4:
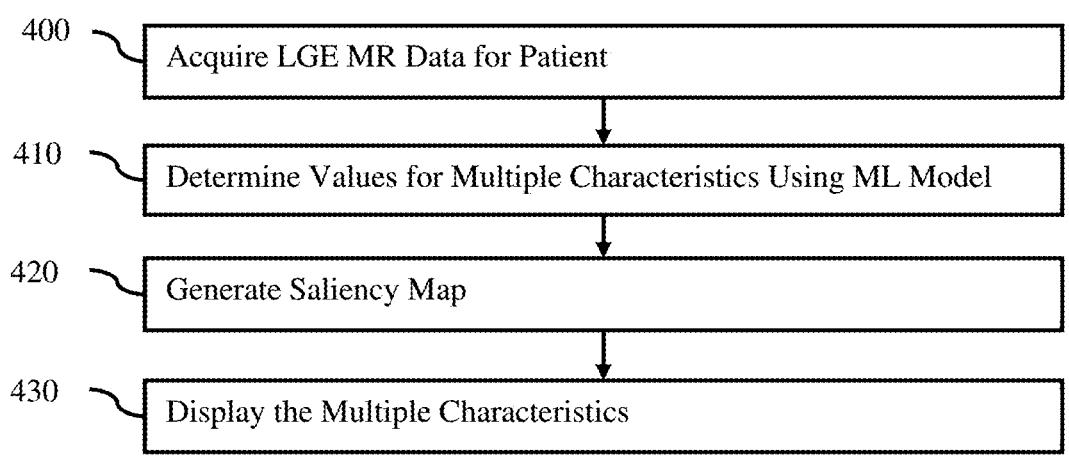
FIG. 4 is a flow chart diagram of one embodiment of a method for LGE analysis in a medical system.

FIG. 4 is a flow chart diagram of one embodiment of a method for LGE analysis for a MR imager. A machine-learned model includes sub-parts separately trained for different tasks. The multi-task, machine-learned model is applied to LGE data 200 for a given patient to output values for the different LGE-related tasks (e.g., extent, type, and/or localization).

Figure 5:
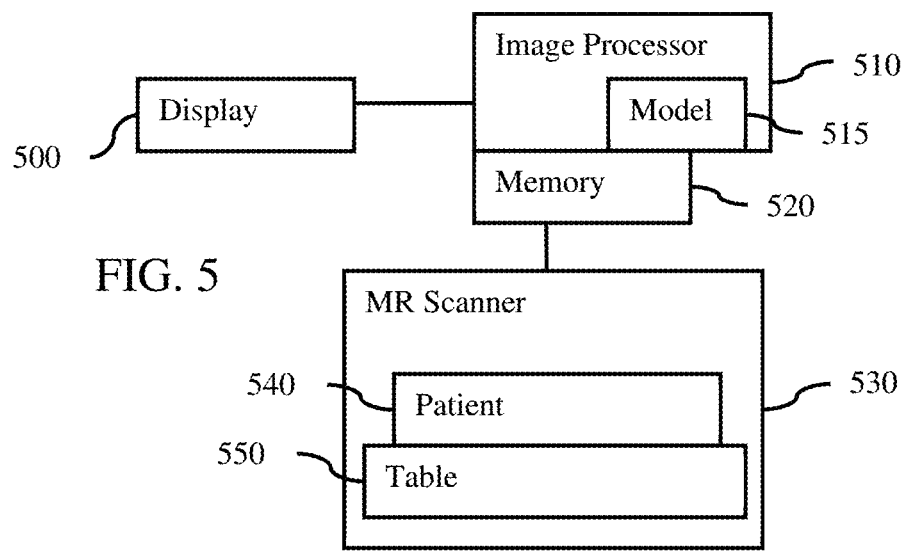
FIG. 5 is a block diagram of one embodiment of a medical system for LGE analysis.

The method of FIG. 4 is performed by the MR scanner or image processor of FIG. 5 or another system. For example, the MR scanner acquires LGE image data. The image processor determines values for cardiac tissue characteristics. The image processor may generate a saliency map. A display, based on an image created by the image processor, displays the values of the characteristics.

The method is performed in the order shown (e.g., top to bottom or numerical), but other orders may be used. Additional, different, or fewer acts may be provided. For example, act 420 is not provided. As another example, acts for configuring the scanning are performed based on user input or other information.

In act 400, an MR scanner acquires LGE MR data representing a patient. The patient is scanned using an LGE MR protocol. The resulting reconstruction and/or image is the LGE MR data. In other embodiments, the LGE MR data is acquired from memory or transfer over a computer network.

Other types of data may be acquired. For example, MR data showing cardiac motion or deformation, or sensor data are acquired.

In act 410, an image processor determines values for multiple LGE-related characteristics of cardiac tissue. For example, (1) an extent of enhancement, (2) a type of enhancement, and/or (3) a localization of enhancement of cardiac tissue are determined. The extent may be determined as a % of a region and/or as a presence or absence of the enhancement. The type may be determined as focal or diffuse. The localization may be determined as whether localized within a wall or not or as a location of localization (e.g., sub-endocardial, epicardial, mid-wall, or transmural).

The image processor determines the values for the characteristics for the whole heart. Alternatively, the values are determined for each of different regions of a heart model. Without segmentation of scar, lesion, or another specific tissue, the values of characteristics for each region of a heart model are determined.

Other information may be determined as well. For example, in addition to determining LGE-related characteristics of cardiac tissue, a disease classification for the heart or cardiac tissue is determined. For example, a class is selected from a group of options, such as no disease, dilated cardiomyopathy (DCM), hypertrophic cardiomyopathy HCM, left ventricular non-compaction cardiomyopathy (LVNC), or another disease.

As another example, the classification is of group membership to identify similar patients. The latent representation 212 is a disease/task-specific patient fingerprint, which may be used to differentiate and classify patient subgroups or perform similarity search (towards "patients-like-mine/me" use cases). Hashing forests or a machine-learned classification network 250 may be used for efficient searching.

In yet another example, the classification is of statistical membership, such as a time-to event (e.g., reoccurrence, readmittance, or death) or event time (e.g., time of survival). The task-specific network or model including the classification network 250 for disease classification may be coupled with statistical methods for time-to-event modelling (e.g., Kaplan-Meier and Cox proportional hazards) or trained to estimate the statistic. The classification network 250 and/or classification 252 are used to obtain predictors on pathophysiologic development and treatment prognosis.

The determination is performed by or using a machine-learned model. The machine-learned model may be a neural network, such as a deep learned neural network. The machine-learned model is a multi-task model, having separate output branches in the architecture. Separate output branches (e.g., one or more decoders, layer structures, or single layers) are provided for each characteristic, such as one for extent, type, and localization of scar tissue. In one embodiment, the deep learned neural network of FIG. 2 is used. The encoder 210 receives the input of the LGE MR data 200 and outputs the latent representation 212. Three decoders 220, 230, 240 form the separate output branches to output the extent 222, type 232, and localization 242 in response to input of the latent representation 212.

The machine-learned model is any machine-learned classifier or network. For example, a neural network is used to regress the relationship between the input LGE data and the output characteristics. A fully connected neural network, convolutional neural network, fully convolutional network, dense net, and/or another neural network may be used. In one embodiment, an image-to-image network (e.g., U-net) is used, such as an encoder-decoder network where the encoder increases abstraction and decreases resolution, providing values for bottleneck features to the decoder for decreasing abstraction and increasing resolution to output a segmentation. A support vector machine, clustering based machine learning, Bayesian, or other machine-learned regressor may be used.

The image processor estimates a value or values for each of multiple characteristics as multiple tasks. The output branches for the different tasks are responsive to the latent representation 212, which is created from input of the LGE MR data to the machine-learned model. The various tasks use the same latent representation 212, allowing joint training and reduced computation in application.

The values are determined in response to input of the LGE image data 200. In other embodiments, other information is input. For example, FIG. 2 shows input of motion image data 202. Images showing motion, such as CINE MR images or a sequence of anatomy images over a period or time, or a sequence of deformation or strain MR images such as tagging, DENSE or SENC, are input to the encoder 210. Alternatively, or additionally, other data may be input, such as sensor data. Sensor data may include ECG, pressure, or other sensors monitoring the patient. Alternatively, or additionally, clinical data, lab test results, calculated quantities (e.g., fraction flow reserve), medical history, family history, and/or other patient-related information may be input. The encoder 210 generates the latent representation 212 from or based on the inputs.

In an embodiment, the processing combines the analysis of myocardial scar from LGE with the analysis of wall motion abnormalities from the aggregated CINE anatomical image series at the corresponding slice or segment locations. The anatomical images may also represent wall thickness, or calculated wall thickness may also be input. Wall thickness and strain parameters can contribute to a jointly performed disease detection or classification task by the classification network 250. The wall motion abnormalities information could be expressed, for example, as myocardial strain parameters. The myocardial strain can be separately extracted by another state-of-the-art method and integrated on a pixel or segment (standardized region) level.

In yet another embodiment, the data processing includes other sensor data, such as ECG signals, body potential maps, etc. The ECG data can be used, for example, to identify the datasets that had been corrupted by arrhythmia, which could be then marked as having unreliable diagnostic quality and not used (i.e., request additional data collection). Different approaches for the efficient integration of multimodal data could be used, such as stacked auto-encoders, which cascade specialized neural networks to pre-process different data sources before performing deep fusion into a common network formed by the encoder 210. Alternative strategies could include task-based losses during the offline network training process, which compute derived clinical cardiac measurements from the images and compare with corresponding original ground truth, to guide attention towards relevant physiological aspects. Losses based on tasks related to the additional data are used to assist in training for the LGE-related characteristic estimation.

The machine-learned model operates based on how the model was trained. Different training results in different values of learnable parameters, so results in different operation. To deal with a lack of accurate segmentations, the machine-learned model being applied was trained using radiology clinical reports with LGE information. This allows creation and application of the machine-learned model despite there being no or only limited segmentation of borders of scars in cardiac tissue available for training.

The machine-learned model was trained for multiple tasks, such as using losses for extent, type, and localization extracted from radiology clinical reports with LGE information. By jointly training based on the multiple task losses, the values of the learnable parameters may be more accurate due to the guidance of multiple characteristics. In a further embodiment, segmentation is available for some of the training samples, so the machine-learned model was trained with loss based, in part, on the segmentation of scar in cardiac tissue where available.

In act 420, the image processor generates a saliency map. Different saliency maps may be generated for the different tasks. At least one of the separate branches of the machine-learned model is used to generate at least one saliency map. Each network head or decoder trained with weak supervision can be used to generate a saliency map that highlights image regions that contributed to the decision (i.e., contribute to the estimated value of the characteristic). The LGE data being input is varied at each location to determine the saliency of that location to the final estimate. The regions having a greater contribution would encompass the scar region(s) and other image features that explain the decision. Saliency may be used in training as well. Further supervision may be provided during training by calculating the loss between saliency maps and scar ground truth maps, when available.

In act 430, a display displays the outputs from application of the machine-learned model. The values output by the model or information derived therefrom may be displayed. The image processor generates an image showing the values. The image may include a representation of the patient's heart, such as an MR image. The values may be annotations on the MR image. The values are communicated to the user by display of the image.

The display is text (e.g., alphanumeric), graph, or highlighting. The extent, type, and localization, with or without other estimates (e.g., class), are displayed. In one embodiment, the display uses a heart model, such as the AHA 16-segment model. FIG. 3 shows an example. Color coding is used to indicate the relative magnitude of one or more of the characteristics. For example, darker highlighting of FIG. 3 indicates greater extent of scarring and no or white highlighting indicates an absence of scarring. Separate models are imaged for the separate characteristics. Alternatively, different aspects of the heart model are modulated by different characteristics, such as color or grayscale for extent, relative region size for type, and position within region of the highlighting for localization.

FIG. 5 shows one embodiment of a medical system for LGE analysis. The medical system includes the display 500, memory 520, and image processor 510. The display 500, image processor 510, and memory 520 may be part of the MR scanner 530, a computer, server, workstation, or other system for image processing medical images from a scan of a patient. A workstation or computer without the MR scanner 530 may be used as the medical system.

Additional, different, or fewer components may be provided. For example, a computer network is included for remote image generation of locally captured LGE data or for local estimation of patient characteristics from remotely captured LGE data. The machine-learned multi-task model is applied as a standalone application on the workstation or a local device or as a service deployed on network (cloud) architecture. As another example, a user input device (e.g., keyboard, buttons, sliders, dials, trackball, mouse, or other device) is provided for user alteration or placement of one or more markers (e.g., landmarks). In yet another example, the medical scanner 530 is not provided.

The LGE data, motion data, sensor data, network definition, values of learned parameters, machine-learned model 515, feature values, values of characteristics, other outputs, display image, and/or other information are stored in a non-transitory computer readable memory, such as the memory 520. The memory 520 is an external storage device, RAM, ROM, database, and/or a local memory (e.g., solid state drive or hard drive). The same or different non-transitory computer readable media may be used for the instructions and other data. The memory 520 may be implemented using a database management system (DBMS) and residing on a memory, such as a hard disk, RAM, or removable media. Alternatively, the memory 520 is internal to the processor 510 (e.g., cache).

The instructions for implementing the training or application processes, the methods, and/or the techniques discussed herein are provided on non-transitory computer-readable storage media or memories, such as a cache, buffer, RAM, removable media, hard drive, or other computer readable storage media (e.g., the memory 520). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code, and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU, or system. Because some of the constituent system components and method steps depicted in the accompanying figures may be implemented in software, the actual connections between the system components (or the process steps) may differ depending upon the manner in which the present embodiments are programmed.

The image processor 510 is a controller, control processor, general processor, digital signal processor, three-dimensional data processor, graphics processing unit, application specific integrated circuit, field programmable gate array, artificial intelligence processor, digital circuit, analog circuit, combinations thereof, or other now known or later developed device for processing LGE MR data. The image processor 510 is a single device, a plurality of devices, or a network of devices. For more than one device, parallel or sequential division of processing may be used. Different devices making up the image processor 510 may perform different functions. In one embodiment, the image processor 510 is a control processor or other processor of the medical scanner 530. The image processor 510 operates pursuant to and is configured by stored instructions, hardware, and/or firmware to perform various acts described herein.

The image processor 510 or another remote processor is configured to train a machine learning architecture. Based on a user provided or other source of the network architecture and training data, the image processor 510 learns to relate one or more input variables (e.g., LGE MR data) to outputs for different tasks in patient modeling. The result of the training is a machine-learned multi-task network for patient modeling.

Alternatively, or additionally, the image processor 510 is configured to apply the multi-task machine-learned model 515. In response to input of LGE MR data, the machine-learned model 515 outputs a value or values for one or more characteristics. The output is based on values determined for features within the model. One or more of these feature values (e.g., the latent representation) are used in other parts (e.g., decoders or other output branches) of the machine-learned model 515 for generating outputs for multiple tasks (e.g., extent of enhancement, type of enhancement, and localization of enhancement). In one embodiment, the image processor 510 is configured to apply the model 515 of FIG. 2, with or without the classification network. Values for multiple cardiac tissue characteristics are output based on a latent representation generated from input data (e.g., LGE data with or without other data such as motion imaging data) for the patient.

The image processor 510 is configured to apply the machine-learned, multi-task network, which was trained using radiology clinical reports with LGE information without segmentation of scars for any or for most of the samples of the training data. Rather than pixel or voxel level segmentation, a heart model with corresponding segments or regions may be used since the clinical reports often reference either the model or anatomy associated with the model. The characteristics for the different tasks are estimated by the model for each of the regions.

The display 500 is a CRT, LCD, projector, plasma, printer, tablet, smart phone or other now known or later developed display device for displaying the output, such as an image of values of the tissue characteristics, image of a heart model, and/or image from the MR scanner 530.

The MR scanner 530 is a diagnostic scanner. The MR scanner 530 operates pursuant to one or more settings to scan a patient 540 resting on a bed or table 550. The settings control scanning including transmission, reception, reconstruction, and image processing. A scanning protocol is followed to generate data representing the patient 540, such as LGE image data representing the heart of the patient. The patient 540 is imaged by the MR scanner 530 using the settings.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for late gadolinium enhancement (LGE) analysis for a magnetic resonance (MR) imager, the method comprising:
   acquiring LGE MR data representing a patient;
   determining (1) an extent of enhancement, (2) a type of enhancement, and (3) a localization of enhancement of cardiac tissue, the determination being by a machine-learned model with separate output branches for the extent, the type, and the localization where the output branches are responsive to a latent representation from input of the LGE MR data to the machine-learned model; and
   displaying the extent, type, and localization.

2. The method of claim 1 wherein determining the extent comprises determining a presence or absence of the enhancement, wherein determining the type comprises determining as focal or diffuse, and wherein determining the localization comprises determining whether localized within a part of the myocardial wall region.

3. The method of claim 1 wherein determining comprises determining by the machine-learned model comprising a deep learnt neural network.

4. The method of claim 3 wherein determining comprises determining with the deep learnt neural network comprising an encoder receiving the input of the LGE MR data and outputting the latent representation and three decoders forming the separate output branches.

5. The method of claim 1 wherein determining further comprises determining a disease classification for the cardiac tissue based on another output branch and the latent representation.

6. The method of claim 1 wherein determining comprises determining the extent, type, and localization for each of multiple regions of a heart model.

7. The method of claim 1 wherein determining comprises determining wherein the machine-learned model was trained using radiology clinical reports with LGE information.

8. The method of claim 7 wherein determining comprises determining where the machine-learned model was trained using the radiology clinical reports with LGE information without segmentation of a boarder of a scar in the cardiac tissue.

9. The method of claim 7 wherein determining comprises determining where the machine-learned model was jointly trained with losses for the extent, type, and localization.

10. The method of claim 9 wherein determining comprises determining where the machine-learned model was jointly trained with the losses for the extent, type, and localization and another loss for a subset of the samples based on segmentation of a scar in the cardiac tissue.

11. The method of claim 1 further comprising generating a saliency map using at least one of the separate branches of the machine-learned model.

12. The method of claim 1 wherein determining comprises determining with input of (a) the LGE MR data and (b) images showing cardiac motion or deformation and/or sensor data to the machine-learned model, the latent representation being based on (a) the LGE MR data and (b) the images showing cardiac motion or deformation and/or sensor data.

13. A medical system for late gadolinium enhancement (LGE) analysis, the medical system comprising:
a memory configured to store LGE data from an MR imager and instructions;
an image processor configured, by execution of the instructions, to apply a machine-learned multi-task network to the LGE data, the machine-learned multi-task network configured to output values for first and second cardiac tissue characteristics in response to the application, wherein the machine-learned multi-task network has separate first and second decoders to output the values for the first and second cardiac tissue characteristics in response to output from a shared encoder; and
a display configured to display the values for the first and second cardiac tissue characteristics.

14. The medical system of claim 13 wherein the machine-learned multi-task network comprises the encoder configured to generate a latent representation of the LGE data and the first and second decoders configured to output the values for the first and second cardiac tissue characteristics, respectively, based on the latent representation.

15. The medical system of claim 13 wherein the first and second cardiac tissue characteristics comprise different ones of extent of enhancement, type of enhancement, and localization of enhancement.

16. The medical system of claim 13 wherein the machine-learned multi-task network further comprises a classifier configured to output a classification of disease in response to the application.

17. The medical system of claim 13 wherein the machine-learned multi-task network is configured to receive the LGE data and cardiac motion imaging data, the output of the values being in response to application to the LGE data and the cardiac motion imaging data.

18. The medical system of claim 13 wherein the machine-learned multi-task network was trained using radiology clinical reports with LGE information without segmentation of scars for most of the samples of the training data.

19. The medical system of claim 13 wherein the image processor is configured to determine the output values for each of a plurality of standardized heart regions.

20. A method for machine training a model, the method comprising:
extracting multiple late gadolinium enhancement (LGE) characteristics of hearts from radiology clinical reports with LGE information for a plurality of patients;
machine training a multi-task model to receive LGE image data, generate latent space data in response to the LGE image data, and output values for the multiple LGE characteristics by separate decoders in response to the latent space data, training data for the machine training including the extracted LGE characteristics as ground truth; and
storing the machine trained multi-task model.

21. The method of claim 20 wherein extracting comprises automated extraction from the radiology clinical reports with LGE information with natural language processing or textual pattern matching.

22. The method of claim 20 further comprising segmenting, by an image processor, scar tissue represented in the LGE data for a subset of the training data, and wherein machine training comprises machine training with first and second tasks of the multi-task model being cardiac tissue characterization and a third task of the multi-task model being segmentation, a loss for the machine training being based on the first and second tasks for the training data without the segmented scar tissue and based on the first, second, and third tasks for the training data with the segmented scar tissue.

* * * * *